(12) United States Patent
Sugarek

(10) Patent No.: US 10,261,339 B2
(45) Date of Patent: Apr. 16, 2019

(54) SKIN CONTACT REDUCTION DEVICE FOR EYEWEAR AND OTHER HUMAN EAR AND TEMPLE RESTING EQUIPMENT

(71) Applicant: Steven Sugarek, Houston, TX (US)

(72) Inventor: Steven Sugarek, Houston, TX (US)

( * ) Notice: Subject to any disclaimer, the term of this patent is extended or adjusted under 35 U.S.C. 154(b) by 0 days.

(21) Appl. No.: 15/622,035

(22) Filed: Jun. 13, 2017

(65) Prior Publication Data

US 2018/0356648 A1    Dec. 13, 2018

(51) Int. Cl.
*G02C 5/00* (2006.01)
*G02C 5/14* (2006.01)
*G02C 5/16* (2006.01)
*A61M 16/06* (2006.01)

(52) U.S. Cl.
CPC .......... *G02C 5/16* (2013.01); *A61M 16/0672* (2014.02); *A61M 16/0683* (2013.01); *G02C 5/001* (2013.01); *G02C 5/14* (2013.01); *A61M 2205/0216* (2013.01)

(58) Field of Classification Search
CPC .......... G02C 5/14; G02C 5/143; G02C 5/146; G02C 5/16; G02C 5/001; G02C 5/02; G02C 5/04; G02C 5/06; G02C 5/10; A61M 16/0672; A61M 16/0683
USPC .................................. 351/117–118, 121–123
See application file for complete search history.

(56) References Cited

U.S. PATENT DOCUMENTS

| | | | | |
|---|---|---|---|---|
| 3,561,472 A | * | 2/1971 | Lamb ...................... | F16K 15/14 137/513.3 |
| 4,852,610 A | * | 8/1989 | McHugh ................ | A62C 37/50 137/271 |
| 5,344,558 A | * | 9/1994 | Kool .................... | B01D 27/106 210/117 |
| 2015/0000016 A1 | * | 1/2015 | Crawford ................ | A61F 9/029 2/423 |
| 2015/0103308 A1 | * | 4/2015 | Williams ............... | G02C 3/003 351/157 |
| 2017/0371177 A1 | * | 12/2017 | Yribarren .............. | G02C 11/00 |

* cited by examiner

*Primary Examiner* — Jordan M Schwartz
(74) *Attorney, Agent, or Firm* — Roy Patrick Norris

(57) ABSTRACT

Embodiments of a skin contact reduction device that is substantially spherically shaped and attaches to the temple portion of facial equipment that goes over the ear or alongside the wearer's face. The device is directionally positioned with a larger opening pointing towards the front of the wearer's face and a smaller opening towards the rear. Both the larger front opening and interior of the device are significantly larger than the width of the temple portion of the facial equipment and therefore the device does not compress or stiffen when installed. The smaller rear opening of the device resiliently grips the temple portion of the facial equipment. Once attached, the device is adjusted by the wearer to a preferred position to keep a wearer's equipment on their face while minimizing contact and pressure between the temple or ear portion of the equipment frame and the wearer's head.

2 Claims, 2 Drawing Sheets

10,261,339 B2

Figure 1:
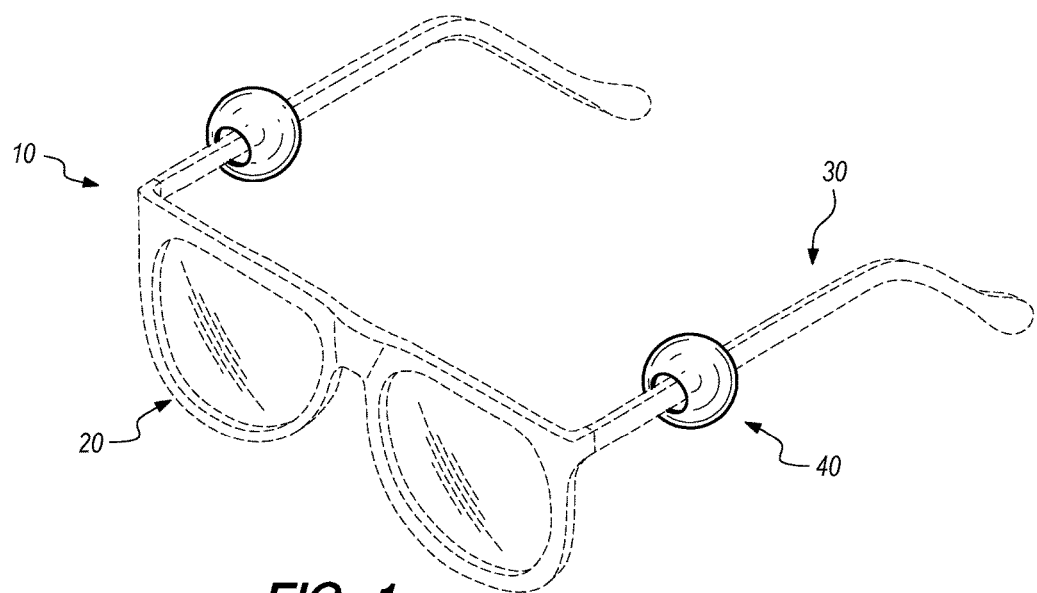

SKIN CONTACT REDUCTION DEVICE FOR EYEWEAR AND OTHER HUMAN EAR AND TEMPLE RESTING EQUIPMENT

CROSS-REFERENCE TO RELATED APPLICATIONS

None.

FEDERALLY SPONSORED RESEARCH

Not applicable.

SEQUENCE LISTING OR PROGRAM

Not applicable.

BACKGROUND

Field of Invention

This invention relates to a device that can be used to reduce contact and pressure between a wearer's skin and facial equipment such as a temple portion of an eyeglass frame or a nose cannula that rests on the wearer's face with an oxygen hose that passes over the wearer's ear.

Prior Art

Relevant prior art includes:
 U.S. Patents
 U.S. Pat. No. 8,733,926 B2—Adjustment Device for Eyeglasses
 U.S. Pat. No. 5,137,342—Eyewear Traction Device
 U.S. Pat. No. 5,790,229—Temple for spectacles
 U.S. Pat. No. 4,563,066—End piece of a spectacle frame earpiece
 U.S. Pat. No. 2,031,771—Temple for Eyeglasses
 D542,832—Non-slipping foam attachment for eyeglasses

BACKGROUND OF THE INVENTION

Often a person who wears eyeglasses or other facial equipment, such as a nose cannula, must endure constant slippage of the equipment or, in many cases, pain of wearing the facial equipment. In the case of eyeglasses, the slippage can manifest itself as the eyeglass frame slipping down the bridge of the nose. If wearing other facial equipment such as a nasal cannula, the wearer can find it difficult to keep the oxygen tubing around the ears and therefore the bridge of the nose cannula attached at the wearer's nose. In both cases, sensitive persons can experience a pressure pain resulting from the contact between the facial equipment and the point on the person's head that is touched by the eye glass frame or cannula hose. Most of the attempts to solve these problems utilize elongated foam pieces through which the facial equipment squeezes through. The foam piece then rests at the side of the wearer's face, or over the wearer's ear. This foam piece attempts to provide both comfort and friction to keep the facial equipment in place. Two U.S. patents summarize the main approaches used to address these problems. U.S. Pat. No. 5,137,342 (1992) to Jannard discloses a common approach whereby a portion of an eyeglasses frame is modified to make the eyeglass frame more comfortable, and in this case, modified to accept a piece of elongated foam. U.S. Pat. No. 8,733,926 B2 (2014) to Stewart does away with a modified eyeglass frame concept altogether and uses only an elongated piece of foam. The foam piece contains a long inner channel sized to compress around the temple of the eyeglass frame. However, neither of these main approaches reduce the surface contact between the wearer's face and the eyeglass temple or nose cannula hose. These foam devices can slip if the wearer is sweating, can be difficult to attach to the facial equipment, are bulky, and apply tremendous pressure to the wearer's ears, temples, or face. This pressure becomes especially unbearable if a wearer suffers from migraine headaches and can only tolerate the smallest amount of pressure against their face. What can appear at first to be soft foam can readily turn into something extraordinarily firm. This is especially true if the facial equipment is passing through an elongated channel in the foam device and causing the foam to compress. The more compressed a foam device is, the denser it becomes and the less soft it feels to a person's head. Instead of the foam device providing a feeling of softness, the wearer instead feels a hard surface pressed up against their face or along the side of their temple, or behind their ear. These prior devices are also not small when compared to the facial equipment they rest upon. Above all, these devices do not minimize contact and pressure between the facial equipment and the wearer's face.

DRAWINGS—FIGURES

FIG. 1—A perspective view of the Skin Contact Reduction Device showing the device in its installed configuration on an embodiment for use with an eyeglass frame.

Figure 2:
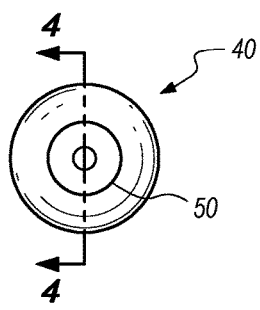

FIG. 2—A front perspective view, of the Skin Contact Reduction Device.

Figure 3:
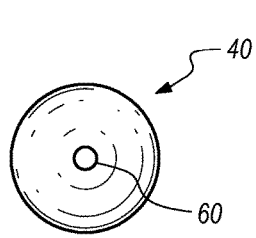

FIG. 3—A back perspective view, of the Skin Contact Reduction Device.

Figure 4:
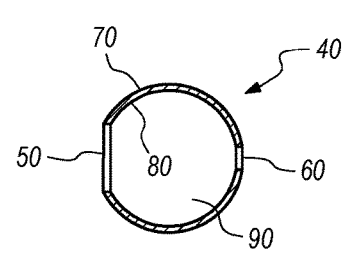

FIG. 4—A cross-sectional view, of the Skin Contact Reduction Device.

Figure 5:
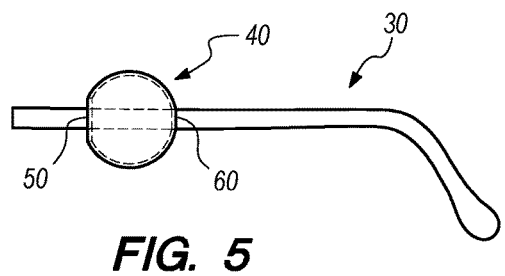

FIG. 5—A perspective view of the Skin Contact Reduction Device in its installed configuration showing the embodiment for an eyeglass frame temple passing therein.

Figure 6:
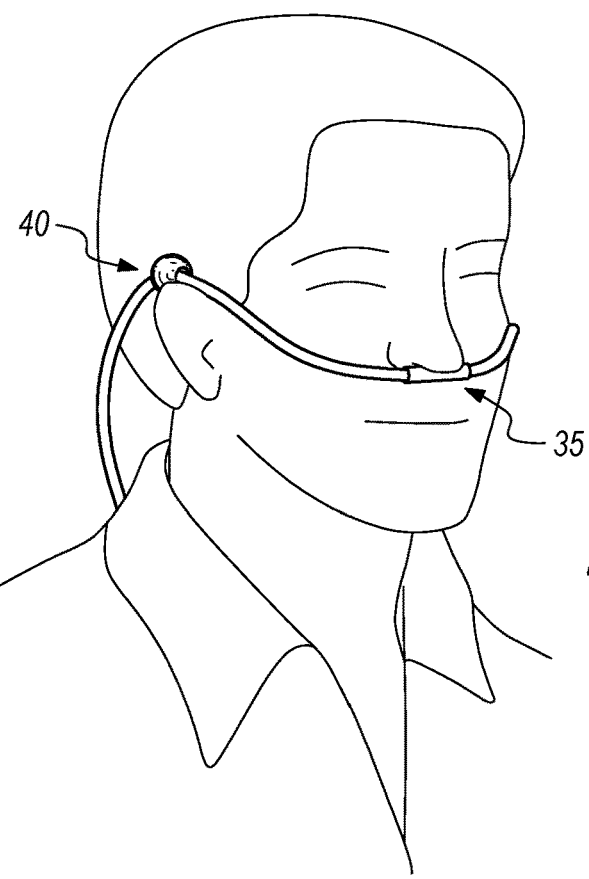

FIG. 6—A perspective view of the Skin Contact Reduction Device showing the device in its installed configuration on an embodiment for use with a nose cannula.

Figure 7:
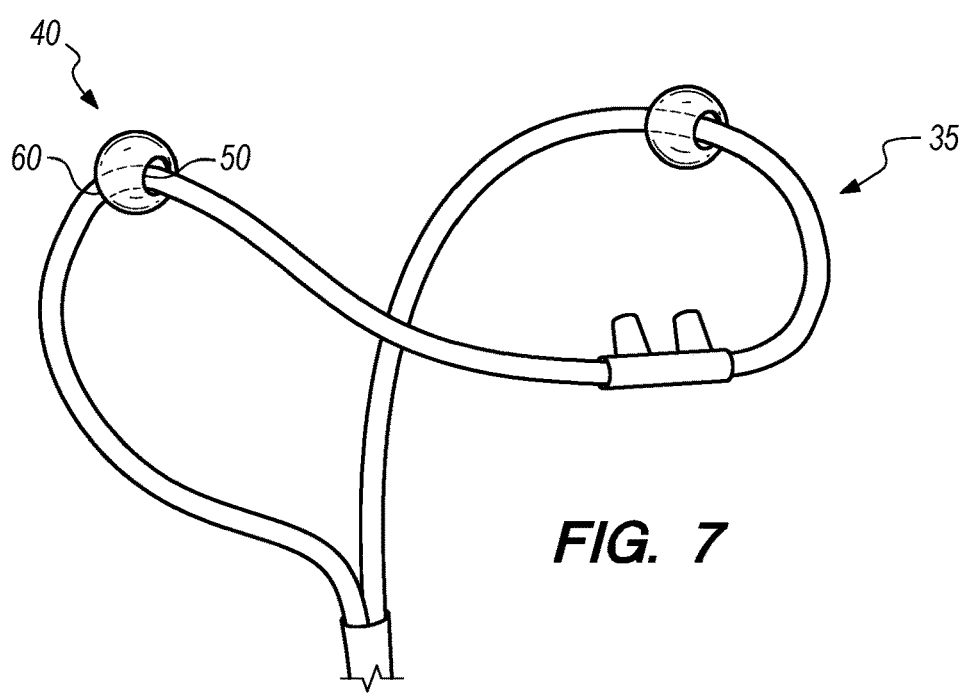

FIG. 7—A perspective view of the Skin Contact Reduction Device in its installed configuration showing the embodiment for a hose of a nose cannula passing therein.

LIST OF REFERENCE NUMERALS

10—eyeglass frame
20—eyeglass lens
30—temple portion of eyeglass frame
35—nose cannula
40—Skin Contact Reduction Device
50—first opening
60—second opening
70—outer surface
80—inner surface
90—interior void

DETAILED DESCRIPTION

As shown in embodiments depicted in FIGS. 1-7, an elastomeric body 40 has an ellipsoidal shape that forms an outer surface 70 and an inner surface 80. Inner surface 80 surrounds and creates an interior void 90. Interior void 90 is terminated at first end with a first opening 50 and at a second end with a second opening 60. As shown in the embodiment depicted in FIGS. 1-5, interior void 90 and first opening 50 are sized to be substantially larger than a cross-sectional width of a temple portion of an eyeglass frame 30. Further, in this embodiment, second opening 60 is sized to be slightly smaller than the cross-sectional width of the temple portion of eyeglass frame 30. Whereas first opening 50 and interior void 90 are sized to not touch the temple of eyeglass frame 30, the size of second opening 60 allows it to resiliently grip the temple of eyeglass frame 30.

In another embodiment depicted in FIGS. 6-7, interior void 90 and first opening 50 are sized to be substantially larger than a cross-sectional width of an oxygen hose that forms a nose cannula 35. In this other embodiment too, second opening 60 is sized to be slightly smaller in diameter than the cross-sectional width of the hose that forms nose cannula 35. In this embodiment as well, whereas first opening 50 and interior void 90 are sized to not touch the hose of nose cannula 35, the size of second opening 60 allows it to resiliently grip the hose of nose cannula 35.

Operation:

As shown in FIGS. 1-5, in operation, elastomeric body 40 is positioned such that the larger first opening 50 is positioned in the direction towards an eyeglass lens 20. The smaller second opening 60 is positioned away from eyeglass lens 20. The temple portion of eyeglass frame 30, that is furthest away from eyeglass lens 20, is inserted into first opening 50. The temple portion of eyeglass frame 30 is then passed through interior void 90 to emerge out from second opening 60. Elastomeric body 40 is then positioned along the temple portion of eyeglass frame 30 to the desired position. Eyeglass frame 30 is then positioned appropriately onto the wearer's face in the normal manner.

As shown in FIGS. 6-7, in operation, elastomeric body 40 is positioned such that the larger first opening 50 is positioned in the direction towards a nose end of nose cannula 35. The smaller second opening 60 is positioned away from the nose end of nose cannula 35. The hose of nose cannula 35, that is furthest away from the nose end of nose cannula 35, is inserted into first opening 50. The hose end of nose cannula 35 is then passed through interior void 90 (as shown in FIG. 4) to emerge out from second opening 60. Elastomeric body 40 is then positioned along the hose of nose cannula 35 to the desired position. Nose cannula 35 is then positioned appropriately onto the wearer's face in the normal manner.

In any of the embodiments, the larger first opening 50 is always passed first onto the wearer's facial equipment with the smaller second opening 60 always following. This directed operation is to prevent elastomeric body 40 from turning inside out during installation onto the wearer's facial equipment.

Advantages:

The present embodiment may have one or more of the following advantages:

One advantage of the embodiments is because elastomeric body 40 has an interior volume 90 and first opening 50 that are substantially larger than the cross-sectional diameters of the facial equipment, the elastomeric body 40 does not compress and become rigid and firm when in its installed configuration but instead retains its soft elastomeric properties.

Another advantage of the embodiments is that elastomeric body 40 has an ellipsoidal shape that serves to minimize surface contact between elastomeric body 40 and the wearer's head.

Another advantage of the embodiments is that elastomeric body 40 only needs to be large enough such that interior volume 90 and first opening 50 are larger than the final attach point of the facial equipment.

I claim:

1. A device to reduce a surface area contact and a pressure between a wearer's skin and a temple portion of a piece of facial equipment that rests on a wearer's face and passes over a wearer's ear comprising: an elastomeric body having an ellipsoidal shape with a first end and a spaced opposed second end, an inner surface, and an outer surface, said first end terminates at a first opening sized to be substantially larger than a cross-sectional width of said temple portion of said facial equipment, said second end terminates at a second opening sized to be slightly smaller than said cross-sectional width of said temple portion of said facial equipment such that said second opening resiliently grips said temple portion of said facial equipment, wherein said inner surface creates an interior void that joins said first opening and said second opening, and said interior void is shaped substantially similar to said outer surface and is sized to be substantially larger than said cross-sectional width of said temple portion of said facial equipment, wherein said ellipsoidal shape of said elastomeric body has an oblate spheroid shape.

2. A device to reduce a surface area contact and a pressure between a wearer's skin and a temple portion of a nose cannula worn on a wearer's face and passing over a wearer's ear comprising: an elastomeric body having an ellipsoidal shape with a first end and a spaced opposed second end, an inner surface, and an outer surface, said first end terminates at a first opening sized to be substantially larger than a cross-sectional width of said temple portion of said nose cannula, said second end terminates at a second opening sized to be slightly smaller than said cross-sectional width of said temple portion of said nose cannula such that said second opening resiliently grips said temple portion of said nose cannula, wherein said inner surface creates an interior void that joins said first opening and said second opening, and said interior void is shaped substantially similar to said outer surface and is sized to be substantially larger than said cross-sectional width of said temple portion of said nose cannula, wherein said ellipsoidal shape of said elastomeric body has an oblate spheroid shape.

* * * * *